United States Patent [19]
Hofheinz et al.

[11] Patent Number: 5,164,293
[45] Date of Patent: Nov. 17, 1992

[54] MONOCLONAL ANTIBODY FOR DETECTING HTLV-I, HTLV-II AND STLV-I VIRUSES

[75] Inventors: David E. Hofheinz, Davie; Gary P. Toedter, Ft. Lauderdale; Lori A. Charie, Hollywood; Samuel R. Pearlman, Davie, all of Fla.

[73] Assignee: Coulter Corporation, Hialeah, Fla.

[21] Appl. No.: 587,725

[22] Filed: Sep. 25, 1990

[51] Int. Cl.⁵ .................................................. C12Q 1/70
[52] U.S. Cl. ........................... 435/5; 530/388.35; 436/518; 436/548; 436/811; 436/813; 435/70.21; 435/172.2; 435/240.27
[58] Field of Search ............ 435/5, 70.21, 172.2, 435/240.27; 436/518, 548; 530/387, 808, 809, 388.35

[56] References Cited

U.S. PATENT DOCUMENTS

| | | |
|---|---|---|
| 4,525,300 | 6/1985 | Yoshida et al. |
| 4,572,800 | 2/1986 | Shimizu et al. |
| 4,588,681 | 5/1986 | Sawada et al. |
| 4,645,738 | 2/1987 | Knowles et al. |
| 4,722,888 | 2/1988 | Broder et al. |
| 4,792,524 | 12/1988 | Miyoshi |
| 4,804,746 | 2/1989 | Yoshida et al. |
| 4,833,071 | 5/1989 | Wang et al. |
| 4,886,743 | 12/1989 | Hood et al. |
| 4,888,290 | 12/1989 | Kortright et al. ............. 435/240.27 |

OTHER PUBLICATIONS

Palker et al., J. Exptl. Med., 159:1117–1131, 1984.
Ishikawa, Clin. Biochem., 20:375–385, 1987.
Ishikawa et al., Int. J. Cancer, 40:233–299, 1987.
Broder et al., Ann. Rev. Immunol., 3:321–326, 1985.
Y. Tanaka et al., Int. J. Cancer, 37:35–42 (1986).

*Primary Examiner*—Esther L. Kepplinger
*Assistant Examiner*—Donna C. Wortman
*Attorney, Agent, or Firm*—Myron C. Cass

[57] ABSTRACT

A hybrid cell line is provided which is capable of producing monoclonal antibodies which binds to HTLV-I and HTLV-II core antigens p24 and p53; but does not bind the p19 core antigen. The antibody also binds to core antigens of simian T-cell leukemia virus Type I (STLV-I). The monoclonal antibody is identified as the KC-88 monoclonal antibody. The cell line which produces the KC-88 monoclonal antibody has been deposited in the American Type Culture Collection, Rockville, Md. and assigned A.T.C.C. Deposit No. HB 10562.

6 Claims, 2 Drawing Sheets

MONOCLONAL ANTIBODY FOR DETECTING HTLV-I, HTLV-II AND STLV-I VIRUSES

FIELD OF THE INVENTION

This invention provides a monoclonal antibody for detecting Human T-Lymphotropic Virus Types I and II (HTLV-I AND -II) antigens, and Simian T-Cell Lymphotropic Virus Type-I (STLV-I) antigen in biological samples and tissue culture media which may contain such antigens and includes an enzyme immunoassay for detecting both HTLV-I and HTLV-II which utilizes said monoclonal antibody.

BACKGROUND OF THE INVENTION

The human T-lymphotropic viruses (HTLV) are members of a family of exogenous human retroviruses. The most widely known human retrovirus is HIV-I human immunodeficiency virus, the AIDS virus. Two HTLV viruses, HTLV-I and HTLV-II, are widely spread; with HTLV-I playing the larger role in illnesses and being especially prevalent in tropical and subtropical environments throughout the world. The HTLV-I virus is associated with adult T-cell leukemia (ATL), tropical spastic paraparesis (TSP)[1] and HTLV-I associated myelopathy (HAM in Japan)[2]. It is characteristic of HTLV-I infection that a period of up to 20 years may pass from the time of infection up to the appearance of symptoms[3]. The HTLV-II virus has been less studied. It has been isolated from some individuals with hairy cell leukemias[4]. While it was not recognized until 1982, hairy cell leukemia is being diagnosed with increased frequency. It affects mainly older adult males with fatigue, malaise, infection (often with atypical organisms), abdominal discomfort, pancyteopenia, splenomegaly and lymphadenopathy[5]. Current research has shown that HTLV-II is endemic in isolated Indian tribes in Central America[11] and frequently occurs in intravenous drug users[12].

Infection with HTLV-I or II can be detected by the presence of antibodies to each of the viruses. Detection techniques include enzyme-linked immunosorbent assays for the detection of antibodies to the virus or to viral components, immunofluorescence and Western blotting. The viruses themselves have been detected by reverse transcriptase activity of culture supernatants, immunofluorescent antibodies directed against viral antigens and sandwich enzyme immunoassays. These techniques are based on studies on the proteins encoded by the HTLV-I and II genomes. The major protein groups are: "tax," whose gene product is a transactivation protein with a molecular weight of 40,000 daltons[6]; "env" (envelope), which has three gene protein products—gp 61, gp 43 and gp 21[6]; "pol," a reverse transcriptase protein, p96[6]; and "gag," which encodes for the major core proteins p53, p24, p19 and p15[6]. The p33 antigen found on HTLV-I has been described as a possible fusion protein of the "gag" and "tax" gene products[10].

Monoclonal antibodies to the HTLV-I virus have been described in the following U.S. Pat. No. 4,722,888 to Broder et al. describes murine monoclonal antibodies to core antigens p19 and p24; U.S Pat. No. 4,886,743 to Hood et al. describes the use of monoclonal antibodies to amino acid sequences within T-cell receptors and particularly within the variable region of the beta chain of the T-cell receptor as markers for disease diagnosis; No. 4,833,071 to Wang et al. describes the detection of HTLV-I antibodies by the use of chemically synthesized peptides having amino acid sequences corresponding to segments of the envelope protein p21; U.S. Pat. No. 4,804,746 to M. Yoshida et al. describes an antibody to a human leukemia virus-related peptide; U.S. Pat. No. 4,792,524 to Miyoshi describes an ATLA cell strain having 44 chromosomes and being useful to produce a ATLA antiserum; U.S. Pat. No. 4,645,738 to Knowles et al. describes two antibodies to leukemia associated antigens in T-cell acute lymphoblastic leukemia, but do not react with the T-cell lymphoma cell line HUT-102; U.S. Pat. No. 4,588,681 to Sawoda et al. describes a process for producing ATLA antigen and a kit for assaying ATLA antibodies, which process uses the known cell strains MT-1, -2, -3 and -4, and especially MT-2; U.S. Pat. No. 4,572,800 to Shimizu et al. describes HTLV related peptides and antibodies to such peptides, particularly an antibody to peptide having an N-terminal peptide chain of p24, which is known as one of the antigenic proteins of ATLA, and is useful as a hapten for p24; and U.S. Pat. No. 4,525,300 to Yoshida et al. describes an antibody of HTLV related peptides and the synthesis of the peptides. In each of the above, an antibody was identified which bound to an antigen of HTLV-I or to a peptide model of some part of HTLV-I; but no single antibody was identified which recognized both HTLV-I and HTLV-II, and which was directed to core antigens.

Monoclonal antibodies to HTLV-I core antigens have also been described in the prior art. Aoki et al. describes an antibody which recognizes the HTLV-I p19 antigen[7]; Cogniaux et al. describe a number of antibodies to p19 or p24 or both[8]; and Palker et al. describes murine monoclonal antibodies to p24[9]. Celluar Products, Inc., Buffalo, N.Y., has developed an assay for detecting antigens of HTLV-I which uses rabbit polyclonal antiserum to HTLV antigen coated on plastic microtiter plates to capture antigen, and a monoclonal antibody to HTLV-I p19 to detect the captured antigen. A drawback to the Cellular Products assay is that the monoclonal antibody utilized recognizes only the p19 core antigen[13]. The p19 core antigen is present in HTLV-I, but is not present in HTLV-II Current research has shown that HTLV-II is an etiologic agent in humans. It would be highly desirable, therefore, to provide a monoclonal antibody which can detect a core antigen common to both HTLV-I and HTLV-II. This invention provides a specific monoclonal antibody and an enzyme linked immunosorbent assay utilizing said monoclonal antibody for detecting HTLV-I and HTLV-II p24 and p53 antigens in biological samples or in a tissue culture media. Also, the invention includes such an immunoassay to the simian T-cell lymphotropic virus type I (STLV-I) p53 and p24 core antigens.

REFERENCES

1. D. Anderson et al., "Licensure of screening tests for antibody to human T-lymphotropic virus type 1," *Morbidity and Mortality Weekly*, Report 37, p. 736 (1988).
2. The Lancet, "HTLV-I Comes of Age," Jan. 30, 1988, pp. 217–219.
3. K. Tajima et al., "Estimation of the rate of incidence of ATL among ATLV (HTLV-1) carriers in Kyushu, Japan," *Jap. J. Clin. Oncol.*, 35:423 et seq. (1985).

4. V. S. Kalyanaraman et al., "A new subtype of human T-cell leukemia virus (HTLV-II) associated with a T-cell variant of Hairy Cell Leukemia.", *Science*, 218:571 (1982).
5. D. P. Stiles et al., *Basic & Clinical Immunology, 6th Ed.*, (Norwalk, Conn.; Appleton & Lange, 1987), p. 397.
6. M. Hatanaka et al., "Genomic expression of human T-lymphotropic virus (HTLV-1).", *AIDS Research*, 2:579 et seq. (1986).
7. T. Aoki et al., "Location of human T-cell leukemia virus (HTLV) p19 antigen on virus-producing cells.", *Int. J. Cancer*, 3: 161 (1984).
8. J. Cogniaux et al., "Production of monoclonal antibodies against HTLV-1 proteins recognizing surface epitopes of live infected cells.", *Leukemia Res.*, 9: 1117 (1985).
9. T. J. Palker et al., "Monoclonal antibodies against human T cell leukemia-lymphoma virus: detection of defective genome and its amplification in MT-Z cells.", *The EMBO J.*, 3: 1339 (1984).
10. N. Kobayashi et al , "Genomic structure of HTLV (human T-cell leukemia virus): detection of defective genome and its amplification in MT-Z cells.", *The EMBO J.*, 3: 1339 (1984).
11. M. Lairmore et al., "Isolation of Human T-Lymphotropic Virus Type 2 from Guaymi Indians in Panama", *PNAS*, in press, 1990.
12. I. Chen et al., "HTLV-I. Prevalence and regulation of gene expression.", *AIDS Research and Human Retroviruses*, 6: 134 (1990).
13. L. Papsidero et al., "Immunodetection of Human T-Cell Lymphotropic Virus Type I core protein in biological samples by using a monoclonal antibody immunoassay", *J. Clin. Microbiol.*, 28: 949 (1990).

SUMMARY OF THE INVENTION

This invention is directed to a cell line produced by hybridoma technology which can produce a monoclonal antibody capable of binding to the HTLV-I and HTLV-II common core antigen p24. The monoclonal antibody also binds to the core antigen p53 but does not bind to core p19. The monoclonal antibody further binds the p33 antigen, which is believed to be a fusion protein arising from "gag" and "tax" gene products. The monoclonal antibody recognizes a common epitope on the p24, p33 and p53 antigens and is identified herein as the KC-88 monoclonal antibody.

The invention further provides an enzyme linked immunoassay for the detection of HTLV-I, HTLV-II AND STLV-I p24 and p53 antigen in either biological samples or in tissue culture media. The assay comprises introducing a predetermined volume of test sample into contact with a solid surface on which is coated a known quantity of said KC-88 monoclonal antibody; incubating the test sample in contact with said coated surface to form a resultant antigen-antibody complex; incubating the resultant complex with a labelled human polyclonal anti-HTLV antibody conjugate, particularly a polyclonal biotin labelled human anti-HTLV antibody, which is capable of yielding a quantitatively measurable signal correlated to a signal for a normal negative test sample with picogram sensitivity of at least approximately 15.6 picograms per milliliter of test sample; contacting the biotin containing antibody-antigen-antibody sandwich with streptavidin peroxidase; adding 3,3',5,5'-tetramethylbenzidine/$H_2O_2$ (TMB) substrate solution; developing color; and determining the optical density of the overall reaction against a predetermined standard to quantitatively determine the presence or absence of HTLV-I, HTLV-II and/or STLV-I. The immunoassay embodying the invention provides a test result of positive or negative relative to the presence or lack thereof of HTLV-1 and/or HTLV-2 respectively. The test results represent a greater degree of accuracy, sensitivity and consistency than has been attainable with known prior art immunoassays.

STATEMENT OF DEPOSIT

Figure 1:
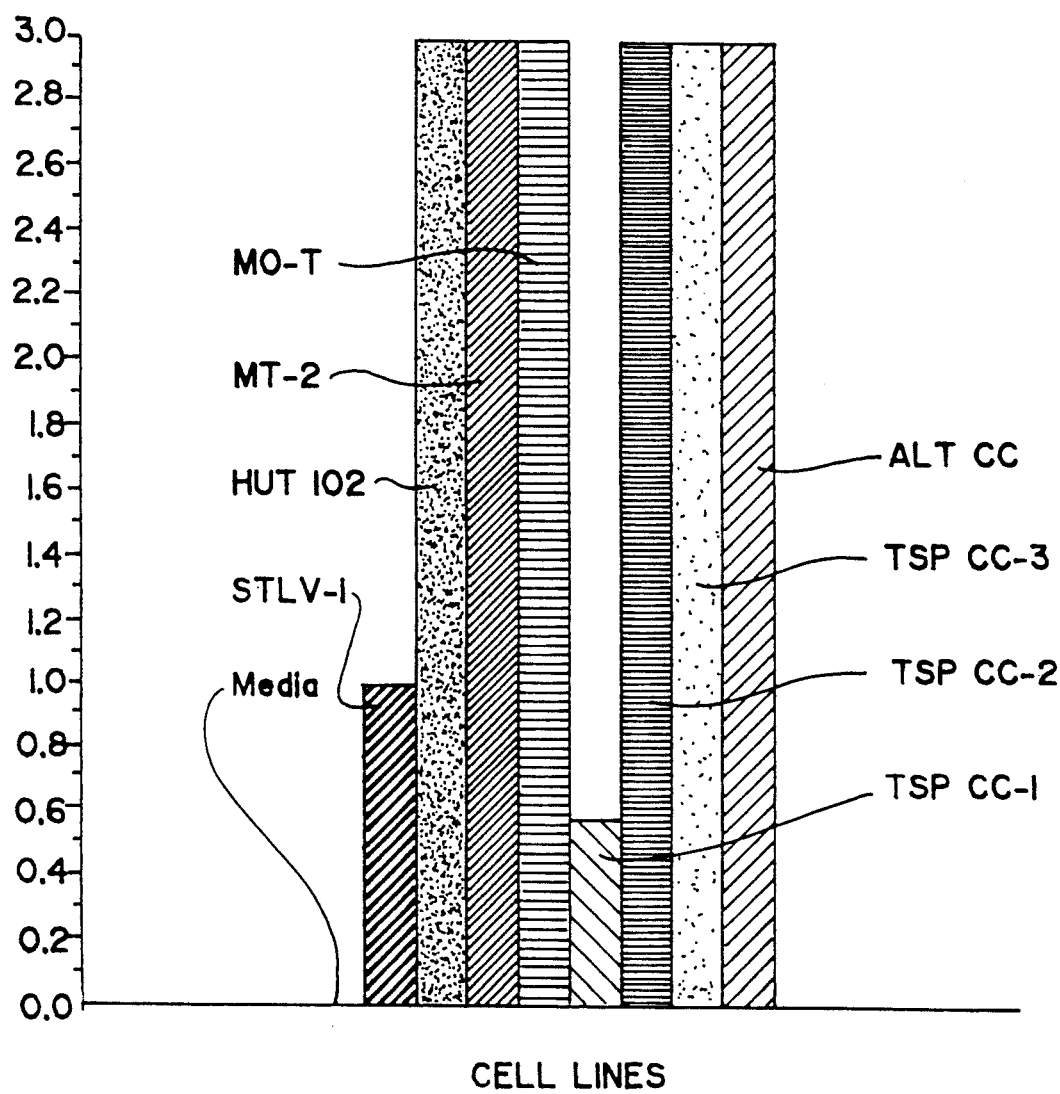
FIG. 1. HTLV-I,-II ELISA Positive Cell Lines.

A hybrid cell line which produces the KC-88 monoclonal antibody embodying this invention has been deposited in the American Type Culture Collection, 12301 Parklawn Drive, Rockville, Md. 20852 and is assigned A.T.C.C. Deposit No. HB 10562.

DESCRIPTION OF SPECIFIC EMBODIMENT

The term "HTLV" without type designation I or II, is used herein to refer to both HTLV-I and HTLV-II, and also, STLV-I.

Monoclonal antibodies useful in the method may be produced using the techniques of Kohler and Milstein, Nature, 265: 495-497 (1975). See also the specific procedures described in U.S. Patent No. 4,888,290 to Kortright et al. which patent procedures are here incorporated by reference. Samples of HTLV antigen preparations are injected into a mouse and, after a sufficient time, the mouse is sacrificed and spleen cells obtained. The spleen cell chromosomes encoding the base sequences for the desired immunoglobulins are immortalized by fusing them with myeloma cells in the presence of a non-ionic detergent such as polyethylene glycol. The resulting cells, which include the fused hybridomas, are then allowed to grow in a selected medium such as HAT medium. The surviving cells in such medium are grown using limiting dilution techniques. The cells are grown in a suitable container, e.g., microtiter wells, and the supernatant is screened for monoclonal antibodies having the desired activity.

While it is known that the method of the present invention is applicable to HTLV-I, HTLV-II and STLV-I antigens in cells, it is not known at this time if these antigens can be detected in sera, plasma and the like. It is possible that such antigens are present in such sera, plasma and the like at very low concentration levels or are bound up in immune complexes. Cultivation of blood samples, be they plasma, serum or separated lymphocytes, may therefore be necessary in order to detect such antigens. Such cultivation and the use of such cultivated samples is within the scope of the present invention. The antigen may also be a HTLV viral gene product or bound to a HTLV viral gene product; or the antigen may be bound to a lymphocyte and is produced as a result of HTLV infection.

Production of the Hybridoma Cell Line and Monoclonal Antibody

The monoclonal antibody KC-88 was developed as follows:

A male BALB/c mouse was immunized with $2 \times 10^6$ HUT 102 cells [Poiesz et al., Proc. Natl. Acad. Sci., 77: 7415-7419 (1980). HUT 102 is a human cell line which is constitutionally infected with HTLV-I.] Twelve days after the first injection, the mouse was immunized with another $2 \times 10^6$ HUT 102 cells. Following this, on days 22 and 30, the mouse was injected with $2 \times 10^6$ lysed HUT 102 cells. A final injection consisting of 15 micrograms of purified HTLV-I virus was administered two months after the initial HUT injection. Three days after administration of the HTLV-I virus, the spleen was removed from th mouse and a single cell suspension of splenocytes was made. The cells were then fused with SP/O-Ag-14 mouse myeloma cells using polyethylene glycol 1500. The fused cells were placed in tissue culture plates and antibody-producing hybridomas were selected for using HAT medium.

Colonies producing antibody to HTLV core antigen were screened and identified by a capture ELISA assay. Purified HTLV-I antigen (advanced Biotechnologies Columbia, Md.) was coated onto a microtiter plate. Culture supernatant from the colonies was added and the presence of antibody binding to the viral antigen was detected using peroxidase conjugated goat anti-mouse immunoglobulins. Those colonies which were found to have such specific antibody were expanded, cloned in soft agar and then injected into pristine-primed BALB/c mice for the production of antibody-containing ascites fluid. As a result of the above screening, the KC-88, was identified which was specific for HTLV antigens.

The isotype of KC-88 monoclonal antibody was determined to be murine IGG1. Western blotting was performed to the determine molecular weight of antigens recognized by KC-88. Lystates of HUT 102 and MO2 (HTLV-II) were employed as the source of antigen for this analysis. The lysates were electrophoresed on a 5 to 15% SDS-polyacrylamide gel and the separated proteins transferred onto nitrocellulose. The KC-88 monoclonal antibody was incubated with th transferred proteins and bound KC-88 monoclonal antibody was detected by autoradiography with $^{125}$I-goat anti-mouse immunoglobulins. The core antigens p53, p33, and p24 (molecular weights 53,000, 33,000 and 24,000 daltons respectively) were specifically recognized by the KC-88 monoclonal antibody. The p19 core antigen was not recognized. Both HTLV-I and HTLV-II antigens were recognized.

An antigen capture ELISA assay was developed suing purified KC-88 monoclonal antibody solid-shaped onto a 96 well microtiter plates as the capture antibody. A 200 μl control or test sample was added to each antibody coated test well, followed by eh addition of 20 μl of lyse buffer. The wells were covered nd the microtiter plate was incubated at 37° C. for 2 hours. The cover was then removed and the plate washed six times. After washing, 200 μl of a biotin labelled human polyclonal anti-HTLV antibody derived from plasma from a patient infected with HTLV-I was added to each well, the plate covered and the whole incubated at 37° C. for 60 minutes. The cover was then removed and the plate washed six times. After washing, 200 μl of streptavidin-horseradish peroxidase was added to each well, the plate covered and the whole incubated at 37° C. for 30 minutes. The cover was then removed and the plate washed six times. After washing, 200 μl of TMB substrate solution was added to each well, the plate covered and the whole incubated at room temperature for 30 minutes. Color developed in both HTLV-I and HTLV-II containing wells, thus indicating that the KC-88 monoclonal antibody recognizes core antigens of both HTLV-I and HTLV-II. The color development was stopped by the addition of 50 μl of CSR-1 to each well. The optical density of the solution was measured at 450 nanometers using a microtiter plate reader versus a standard or blank, to quantify the assay.

Figure 2:
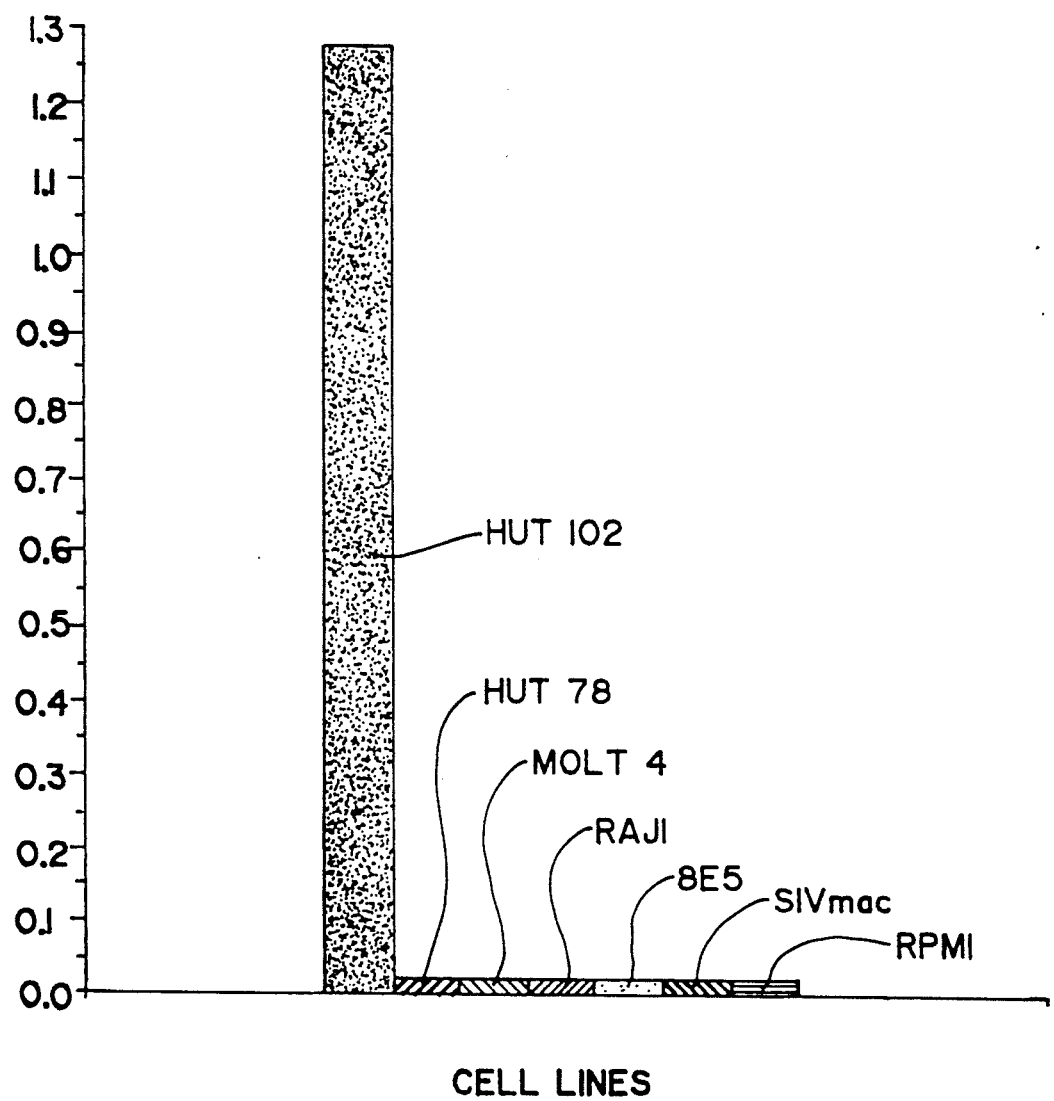
FIG. 2. HTLV-I,-II ELISA Negative Cell Lines.

The specificity of this assay was determined in another series of tests using culture supernatants from a variety of cells. These results are summarized in FIGS. 1 and 2 and Table 1. All cell lines which express HTLV-I, HTLV-II or STLV-I were positive in this assay. All other cell lines were negative.

TABLE 1

| Specificity of Antigen Capture ELISA | |
|---|---|
| Cell Line | Results |
| HUT 102 (HTLV-I) | + (positive) |
| MT2 (HTLV-I) | + |
| C5/MJ (HTLV-I) | + |
| MOB (HTLV-II) | + |
| MOT (HTLV-II) | + |
| STLV-I | + |
| HUT 78/SIVmac-251) | − (negative) |
| 8E5 (HTLV-III, HIV-I) | − |
| HUT 78 (uninfected) | − |
| MOLT 4 (uninfected) | − |
| Raji (EBV infected) | − |
| CMV | − |
| Herpes I and II | − |

As a further example of the utility of the KC-88 monoclonal antibody and the assay of the present invention, peripheral blood lymphocytes from a variety of HTLV-I or II infected patients were cultured. Assay test results, Table 2, indicate that the antigen capture ELISA can detect HTLV-I or II antigen present in these cultures. An assay method which would not recognize HTLV-II would not detect antigen in a number of the cultures tested in Tables 1 and 2.Further, the assay method indicates that STLV-I antigens can be recognized, thus paving the way for the possible use of this virus in studies utilizing animal models for HTLV-I infection.

TABLE 2

| Antigen Detection in Cultures of Peripheral Blood Lymphocytes (PBL) | |
|---|---|
| Source | Result |
| ATL (HTLV-I) | + (positive) |
| H2E (HTLV-II) | + |
| H2G (HTLV-II) | + |
| Pan 012 (HTLV-II) | + |
| PHA-P Stimulated | − (negative) |

The precision and sensitivity of the assay method was determined using core antigen p24 from HUT 102 cultures and purified by affinity chromatography. The concentration of the antigen in a given solution was determined by protein assay. The antigen was then titered to its endpoint to determine the sensitivity of the assay. The assay was found sensitive down to a concentration of approximately 16 picograms per milliliter. The results are shown in Table 3.

TABLE 3

| Sensitivity of Antigen Capture ELISA | |
|---|---|
| Antigen Conc. (pg/ml) | Absorbance (450 nm) |
| 250.0 | 1.496 |
| 125.0 | 0.763 |
| 65.5 | 0.383 |
| 31.3 | 0.200 |
| 15.6 | 0.114 |
| 0.0 | 0.035 |

To determine the reproducibility of the assay from day to day, the standard curve was assayed repeatedly in ten separate assays over a ten day time period. The mean optical density, standard deviation, and percent coefficient of variation (CV) then calculated. The results are shown in Table 4.

TABLE 4

HTLV-I,II ELISA Inter-Assay Precision Profile

| Antigen (ng/mL) | n | Mean | Std. Dev. | CV |
|---|---|---|---|---|
| 0.250 | 101 | 1.496 | 0.118 | 7.9% |
| 0.125 | 101 | 0.763 | 0.080 | 10.5% |
| 0.063 | 102 | 0.383 | 0.051 | 13.3% |
| 0.031 | 102 | 0.200 | 0.038 | 18.8% |
| 0.016 | 102 | 0.114 | 0.027 | 23.9% |
| SLOPE | 102 | 5.899 | 0.455 | 7.7% |

To determine the uniformity of a single assay, the standard curve was assayed repeatedly (n=12 per point) on a single plate. The mean optical density, standard deviation, and percent coefficient of variation were then calculated. The results are shown in Table 5.

TABLE 5

HTLV-I,II-ELISA Inter-Assay Precision Profile

| Antigen (ng/mL) | n | Mean | Std | CV |
|---|---|---|---|---|
| 0.250 | 12 | 1.516 | 0.052 | 3.40% |
| 0.125 | 12 | 0.775 | 0.037 | 4.78% |
| 0.063 | 12 | 0.359 | 0.019 | 5.25% |
| 0.031 | 12 | 0.181 | 0.011 | 5.98% |
| 0.016 | 12 | 0.095 | 0.007 | 7.18% |
| SLOPE | 12 | 6.111 | 0.210 | 3.43% |

The above results indicate that the assay of the present invention, using the KC-88 monoclonal antibody, recognizes antigen from both HTLV-I and HTLV-II infected individuals, can recognize STLV-I antigen, does not recognize antigens from non-HTLV-I or -II and non-STLV-I strains, and is extremely sensitive, with sensitivity extending into the lower (<25) picogram range.

THE IMMUNOASSAY EMBODIMENT

The KC-88 monoclonal antibody is used in an immunoassay for detecting a HTLV-I, HTLV-II and STLV-I antigen, the KC-88 antigen, in biological samples and tissue culture media which may contain said antigens. The assay comprises introducing a predetermined volume of test sample into contact with a solid surface to which is bound a known quantity of a monoclonal antibody capable of binding to a common epitope of an antigen of HTLV-I, HTLV-II and STLV-I p24, p33 and p53 core antigens without binding the p19 core antigen; incubating the test sample in contact with said surface to form a resultant antigen-antibody complex, complex A, in contact with said solid surface; decanting the test sample and washing the surface to remove residual test sample; contacting the complex A coated surface with a biotin labelled polyclonal anti-HTLV antibody solution; incubating the polyclonal antibody-complex A mixture to form a labelled polyclonal antibody-antigen-monoclonal antibody sandwich complex, complex B; decanting the polyclonal antibody solution and washing the surface to remove residual solution; contacting complex B with streptavidin peroxidase and incubating the mixture to form a streptavidin-biotin labelled complex, complex C; decanting the streptavidin peroxidase solution and washing the surface to remove residual solution; adding 3, 3', 5, 5'- tetramethylbenzidine/$H_2O_2$ substrate solution to develop color; stopping color development by the addition of a stopping solution; measuring the optical density of the color; and determining the presence and amount of antigen in the biological sample or tissue culture by means of a reference or standard.

We claim:

1. A hybridoma cell line which produces a monoclonal antibody which specifically binds to an epitope of an antigen common to human T-cell lymphotropic viruses type I and II, which cell line is on deposit with the American Type Culture Collection and assigned A.T.C.C. Deposit No. HB 10562.

2. The monoclonal antibody produced from the cell line having a A.T.C.C. Deposit No. HB 10562.

3. A monoclonal antibody which specifically binds to an antigenic determinant of the HTLV-I, HTLV-II and STLV-I p24, p33 and p53 core antigens, and does not bind to the p19 core antigen, said monoclonal antibody binding the same epitope as the monoclonal antibody produced by the hybridome cell line identified by A.T.C.C. Deposit No. HB 10562.

4. An immunoassay for detecting HTLV-I and HTLV-II antigens in biological samples and tissue culture media, said assay comprising:

(a) introducing a predetermined volume of test sample into contact with a solid surface to which is bound a known quantity of a monoclonal antibody that specifically binds to a common epitope of HTLV-I and HTLV-II p24, p33 and p53 core antigens and does not bind to the p19 core antigen, said monoclonal antibody binding the same epitope as the monoclonal antibody produced by the hybridoma cell line identified as A.T.C.C. Deposit No. HB 10562;

(b) incubating said test sample in contact with said surface to form resultant antigen-antibody complexes;

(c) incubating the resultant complexes and subjecting same to a labelled human polyclonal anti-HTLV antibody which is capable of yielding a quantitatively measurable signal correlated to the signal for a normal negative test sample; and (d) determining the presence and amount of antigen in the sample by an analytical means utilizing said label.

5. The immunoassay of claim 4 wherein simian T-leukemia virus type 1 is detected.

6. A hybridoma cell line which produces a monoclonal antibody which specifically binds to a common antigenic determinant of HTLV-I, HTLV-II and STLV-I p24, p33 and p53 core antigens, and does not bind to the p19 core antigen, said cell line producing a monoclonal antibody which binds to the same epitope as does the monoclonal antibody produced by A.T.C.C. Deposit No. HB 10562.

* * * * *

UNITED STATES PATENT AND TRADEMARK OFFICE
CERTIFICATE OF CORRECTION

PATENT NO. : 5,164,293

DATED : November 17, 1992

INVENTOR(S) : David E. Hofheinz, Gary P. Toedter, Lori A. Charie and Samuel R. Pearlman It is certified that error appears in the above-identified patent and that said Letters Patent is hereby corrected as shown below:

Column 5, line 15, change "advanced" to --Advanced--;

line 28, change "IGG1" to --IgG1--;

line 35, after "with" change "th" to --the--;

line 45, change "suing" to --using--;

line 45, change "solid-shaped" to --solid-phased--;

line 48, after "by" change "eh" to --the--;

line 49, after "covered" change "nd" to --and--;

UNITED STATES PATENT AND TRADEMARK OFFICE
CERTIFICATE OF CORRECTION

PATENT NO. : 5,164,293

DATED : November 17, 1992

INVENTOR(S) : David E. Hofheinz, Gary P. Toedter, Lori A. Charie and Samuel R. Pearlman It is certified that error appears in the above-indentified patent and that said Letters Patent is hereby corrected as shown below:

Column 6, line 19, change "HUT 78/SIVmac-251)" to --HUT 78/SIVmac-251--.

Signed and Sealed this

Twenty-third Day of November, 1993

Attest:

BRUCE LEHMAN

Attesting Officer

Commissioner of Patents and Trademarks